United States Patent
Sobotka (10) Patent No.: US 10,292,754 B2
(45) Date of Patent: May 21, 2019

(54) THERAPEUTIC RENAL NEUROMODULATION FOR TREATING DYSPNEA AND ASSOCIATED SYSTEMS AND METHODS

(75) Inventor: Paul A. Sobotka, West St. Paul, MN (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 1366 days.

(21) Appl. No.: 13/884,602

(22) PCT Filed: Nov. 16, 2011

(86) PCT No.: PCT/US2011/061019
§ 371 (c)(1),
(2), (4) Date: Oct. 3, 2013

(87) PCT Pub. No.: WO2012/068268
PCT Pub. Date: May 24, 2012

(65) Prior Publication Data
US 2014/0024959 A1     Jan. 23, 2014

Related U.S. Application Data

(60) Provisional application No. 61/414,499, filed on Nov. 17, 2010.

(51) Int. Cl.
*A61B 18/14*     (2006.01)
*A61B 18/02*     (2006.01)
(Continued)

(52) U.S. Cl.
CPC .............. *A61B 18/14* (2013.01); *A61B 5/082* (2013.01); *A61B 5/4848* (2013.01); *A61B 18/02* (2013.01);
(Continued)

(58) Field of Classification Search
CPC .......... A61B 2018/00511; A61B 18/02; A61B 18/14; A61B 18/1492; A61B 2018/00434;
(Continued)

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| KR | 20090116492 | 11/2009 |
| WO | WO-199407446 | 4/1994 |

(Continued)

OTHER PUBLICATIONS

A. Vazir et al. "A high prevalence of sleep disorded breathing in men with mild symptomatic chronic heart failure due to left ventricular systolic dysfunction". European Journal of Heart Failure. vol. 9. 2007. p. 243-250. Online. Oct. 6, 2016. <https://onlinelibrary.wiley.com/doi/abs/10.1016/j.ejheart.2006.08.001>.*
(Continued)

*Primary Examiner* — Daniel W Fowler
*Assistant Examiner* — Sean W Collins (57) ABSTRACT

Methods for treating dyspnea with therapeutic renal neuromodulation and associated system and methods are disclosed herein. One aspect of the present technology, for example, is directed to methods that block, reduce, and/or inhibit renal sympathetic nerve activity to achieve a reduction in central sympathetic tone. Renal sympathetic nerve activity may be altered or modulated along the afferent and/or efferent pathway. The achieved reduction in central sympathetic tone may carry therapeutic benefits for patients with dyspnea.

12 Claims, 6 Drawing Sheets

(51) Int. Cl.
*A61B 5/08* (2006.01)
*A61B 5/00* (2006.01)
*A61B 18/00* (2006.01)

(52) U.S. Cl.
CPC ............... *A61B 18/1492* (2013.01); *A61B 2018/00434* (2013.01); *A61B 2018/00577* (2013.01); *A61B 2018/00589* (2013.01); *A61B 2018/00613* (2013.01)

(58) Field of Classification Search
CPC ........... A61B 2018/00577; A61B 2018/00589; A61B 2018/00613; A61B 5/082; A61B 5/484
See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,939,346 B2 | 9/2005 | Kannenberg et al. |
| 6,949,097 B2 | 9/2005 | Stewart et al. |
| 6,951,217 B2 | 10/2005 | Berthon-Jones |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,622,304 B2 | 11/2009 | Tonnessen et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0167509 A1 | 8/2004 | Taimisto |
| 2004/0215186 A1 | 10/2004 | Cornelius et al. |
| 2005/0065567 A1 | 3/2005 | Lee et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212076 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0077201 A1 | 3/2008 | Levin et al. |
| 2008/0086185 A1 | 4/2008 | Amurthur et al. |
| 2008/0255642 A1* | 10/2008 | Zarins ............... A61B 18/1206 607/99 |
| 2008/0319513 A1 | 12/2008 | Pu et al. |
| 2009/0036948 A1 | 2/2009 | Levin et al. |
| 2010/0070004 A1* | 3/2010 | Hlavka ............... A61N 1/3601 607/62 |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |

(56) References Cited

U.S. PATENT DOCUMENTS

| | | |
|---|---|---|
| 2012/0130289 A1 | 5/2012 | Demarais et al. |
| 2012/0130345 A1 | 5/2012 | Levin et al. |
| 2012/0172837 A1 | 7/2012 | Demarais et al. |

FOREIGN PATENT DOCUMENTS

| | | |
|---|---|---|
| WO | WO-1995025472 | 9/1995 |
| WO | WO-9531142 | 11/1995 |
| WO | WO-1997036548 | 10/1997 |
| WO | WO-1999/00060 | 1/1999 |
| WO | WO-2001022897 | 4/2001 |
| WO | WO-2001070114 | 9/2001 |
| WO | WO-2003022167 | 3/2003 |
| WO | WO-2004032727 | 4/2004 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO-2008049084 | 4/2008 |
| WO | WO-2012068268 | 5/2012 |

OTHER PUBLICATIONS

Miller, Reed, "Finding a Future for Renal Denervation with Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European Patent No. 2465470, Granted Oct. 28, 2015, Date of Opposition Jul. 27, 2016, 34 pp.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Supplementary European Search Report dated Apr. 13, 2015; European Application No. 11841336.8; 5 pages.
Kara et al., "Chemoreflexes—physiology and clinical implications." Acta Physio Scand, 2003, 8 pages.
Kentaro et al., "Assessment of central chemosensitivity and cardiac sympathetic nerve activity using I-123 MIBG imaging in central sleep apnea syndrome in patients with dilated cardiomyopathy." Annals of Nuclear Medicine, vol. 21, No. 1, 73-78, 2007.
Pieper et al., "Design and Implementation of a New Computerized System for Intraoperative Cardiac Mapping." Journal of Applied Physiology, 1991, vol. 71, No. 4, pp. 1529-1539.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
Sobotka, Paul et al., "Impaired Hypoxis Ventilatory Drive in Diabetic Patients with Autonomic Neuropathy." J. Clin. Endocrinol. Metab., vol. 62, 1986, 7 pages.
Solin, Peter et al., "Peripheral and Central Ventilatory Responses in Central Sleep Apnea with and without Congestive Heart Failure." Am. J. Respir. Crit. Care. Med., vol. 162, 2000, 7 pages.
U.S. Appl. No. 60/852,787, filed Oct. 18, 2006, 112 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,24, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards[TM]" Edison Awards: Honoring Innovations & Innovators, 2013, 2 pages, <http://www.edisonawards.com/Awards.php>.

(56) References Cited

OTHER PUBLICATIONS

"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals from the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G. F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, dated Jan. 29, 2003, 23 pages.
Gertner, Jon, "Meet the Tech Duo That's Revitalizing the Medical Device Industry." FAST COMPANY, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Intery Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association* White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.

Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients with Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot$^{TM}$ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.

(56) References Cited

OTHER PUBLICATIONS

Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: The EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Allen, E. V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361 ;9.

Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I. H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M. P. et al., "Renal Denervation as a Therapeutic Approach for Hypertension: Novel Implications for an Old Concept," Hypertension, 2009; 54:1195-1201.
Schlaich, M. P. et al., "Renal Sympathetic-Nerve Ablation for Uncontrolled Hypertension," N Engl J Med 2009; 361(9): 932-934.
Smithwick, R. H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):91 1-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter, "Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.

(56) References Cited

OTHER PUBLICATIONS

Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages, <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 : 484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
European Search Report for European Application No. 13159256, dated Oct. 17, 2013, 6 pages.
International Search Report and Written Opinion for International App. No. PCT/US2011/061019, dated Feb. 28, 2012, 10 pages.

* cited by examiner

THERAPEUTIC RENAL NEUROMODULATION FOR TREATING DYSPNEA AND ASSOCIATED SYSTEMS AND METHODS

CROSS-REFERENCE TO RELATED APPLICATION(S)

This application claims the benefit of U.S. Provisional Application No. 61/414,499, filed Nov. 17, 2010, and incorporated herein by reference in its entirety.

TECHNICAL FIELD

The present technology relates generally to renal neuromodulation and associated systems and methods. In particular, several embodiments are directed to therapeutic renal neuromodulation to treat dyspnea and using a measure of chemosensitivity as an indication of central sympathetic hyperactivation.

BACKGROUND

Dyspnea is the subjective sensation of breathlessness. More specifically, dyspnea is defined by the American Thoracic Society as the "subjective experience of breathing discomfort that consists of qualitatively distinct sensations that vary in intensity. The experience derives from interactions among multiple physiological, psychological, social, and environmental factors, and may induce secondary physiological and behavioral responses." Dyspnea itself is a limiting symptom or a significant component of the clinical features associated with systolic heart failure, diastolic heart failure, most phases of chronic kidney disease, panic disorders, chronic lung disease, asthma, hypertension, and both acute and chronic deconditioning.

Current therapies for dyspnea include non-pharmacological and pharmacological approaches. Examples include breathing and meditation techniques, administration of oxygen, morphine, or anti-anxiety medications such as lorazepam. A therapy that substantially ameliorates dyspnea would have broadly applicable, clinically significant, and physiologically important implications.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology is directed to methods for therapeutic renal neuromodulation for the treatment of dyspnea and associated systems and devices. The present disclosure further describes methods for indicating a measure of central sympathetic state by measuring $pCO_2$ sensitivity. The following disclosure includes five sections directed to various aspects of the disclosed technology. Section I, for example, describes renal neuromodulation, and Section II focuses on the pertinent anatomy and physiology. Section III describes techniques for measuring sympathetic activity and associated systems and methods, and Section IV is directed to chronic sympathetic activation and its relationship to dyspnea. Section V describes using therapeutic renal neuromodulation to reduce central sympathetic drive and sympathetic neural activity in a manner that may treat patient for dyspnea and how hypercapnic ventilatory response can be used as an indicator of sympathetic activation.

Specific details of several embodiments of the technology are described below with reference to FIGS. 1-6. Although many of the embodiments are described below with respect to devices, systems, and methods for therapeutic renal neuromodulation, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-6.

The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

I. Renal Neuromodulation

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). As described in greater detail herein, renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics. Additionally, osteoporosis can be sympathetically activated and might benefit from the downregulation of sympathetic drive that accompanies renal neuromodulation.

Various techniques can be used to partially or completely incapacitate neural pathways, such as those innervating the kidney. The purposeful application of energy (e.g., electrical energy, thermal energy) to tissue can induce one or more desired thermal heating effects on localized regions of the renal artery and adjacent regions of the renal plexus, which lay intimately within or adjacent to the adventitia of the renal artery. The purposeful application of the thermal heating and cooling effects can achieve neuromodulation along all or a portion of the renal plexus.

II. Pertinent Anatomy and Physiology

The following discussion provides various details regarding pertinent patient anatomy and physiology. This section is intended to provide additional context regarding the disclosed technology and the therapeutic benefits associated with renal denervation, and to supplement and expand upon the disclosure herein regarding the relevant anatomy and physiology. For example, as mentioned below, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. Autonomic Nervous System

The autonomic nervous system (ANS) is comprised of the parasympathetic and sympathetic nervous systems. These systems work together to regulate visceral body functions including heart rate, blood pressure, respiration, digestion, body temperature, and urination. The ANS is always active at a basal level, primarily acting in an involuntary, reflexive manner to maintain homeostasis. The sympathetic and parasympathetic nervous systems involve networks of nerves connecting the brain, the spinal cord and the peripheral organs. These two systems regulate visceral body functions including respiration, cardiovascular activity, and energy balance.

B. Sympathetic Nervous System

The Sympathetic Nervous System (SNS) is a branch of the autonomic nervous system along with the enteric nervous system and parasympathetic nervous system. Activation of the SNS is typically associated with a "fight or flight" quick alarm or stress response that enables the body to perform strenuous physical activity, such as when fleeing from danger. Within seconds, the heart pumps more forcefully, the heart rate increases, blood is shunted from the GI tract to active muscles and the brain, and blood glucose increases to provide energy for increased cellular metabolism. Sympathetic drive is also a key regulator of the body's blood pressure and fluid balance, ensuring adequate blood supply for vital organs such as the brain when the body is fleeing from danger.

The SNS is balanced by the functions of the "rest and digest" parasympathetic nervous system (PNS), which promotes nutrient absorption from the GI tract and energy storage. While the SNS responds within seconds to environmental triggers, some effects of the parasympathetic nervous system may not be seen for hours. Most visceral organs have both sympathetic and parasympathetic innervation, though one system can dominate control of a given organ. The response to activation of the SNS and PNS is both neuronally and hormonally mediated. The hormonal contribution comes from the adrenal gland, which is activated by the SNS and PNS to release hormones such as epinephrine (adrenaline) into the bloodstream that can amplify the body's response to the neural stimulation. Together, the functions of the sympathetic and parasympathetic nervous systems enable the body to respond to environmental stimuli in a graded fashion instead of simply on or off.

Figure 1:
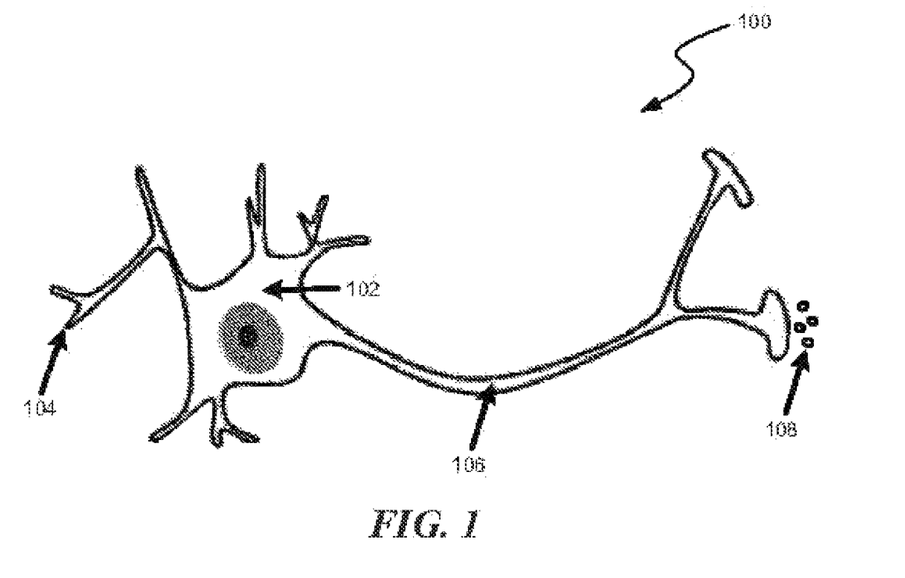
FIG. 1 is a schematic illustration of a human neuron.

The SNS is composed primarily of neurons. As shown in FIG. 1, for example, neurons 100 are composed of three parts: the cell body 102 where information is integrated, specialized projections 104 (i.e., dendrites) that bring information into the cell body 102, and a single projection 106 (i.e., axon) that takes information away from the cell body information is passed between neurons electrochemically across synapses, small gaps between axons 106 and dendrites 104. At a distal end of the pre-synaptic neuron's axon 106, chemicals termed neurotransmitters 108 are released, cross the synapse, and bind to cell surface receptors at a post-synaptic neuron (not shown). An electric potential is generated in the post-synaptic dendrite and spreads to the cell body, where the signal is integrated. The signal relayed to the next neuron (not shown) by generating an electrical potential that travels down the corresponding axon, activating release of neurotransmitters at the distal end of the axon into the next synapse.

Axons are typically bundled together like the ropes of a cable; a large bundle can be visible to the naked eye and is often called a nerve fiber. A cluster of neurons and synapses is called a ganglion. Ganglions provide key relay points throughout the sympathetic nervous system. Although nerve signals may travel from one ganglia to another, many signals pass through only one ganglion. When considering the general ANS architecture, post-ganglionic neurons are those neurons that have their cell bodies in the ganglia and send axons directly out to the peripheral organs. All other neurons are termed pre-ganglionic neurons.

Figure 2:
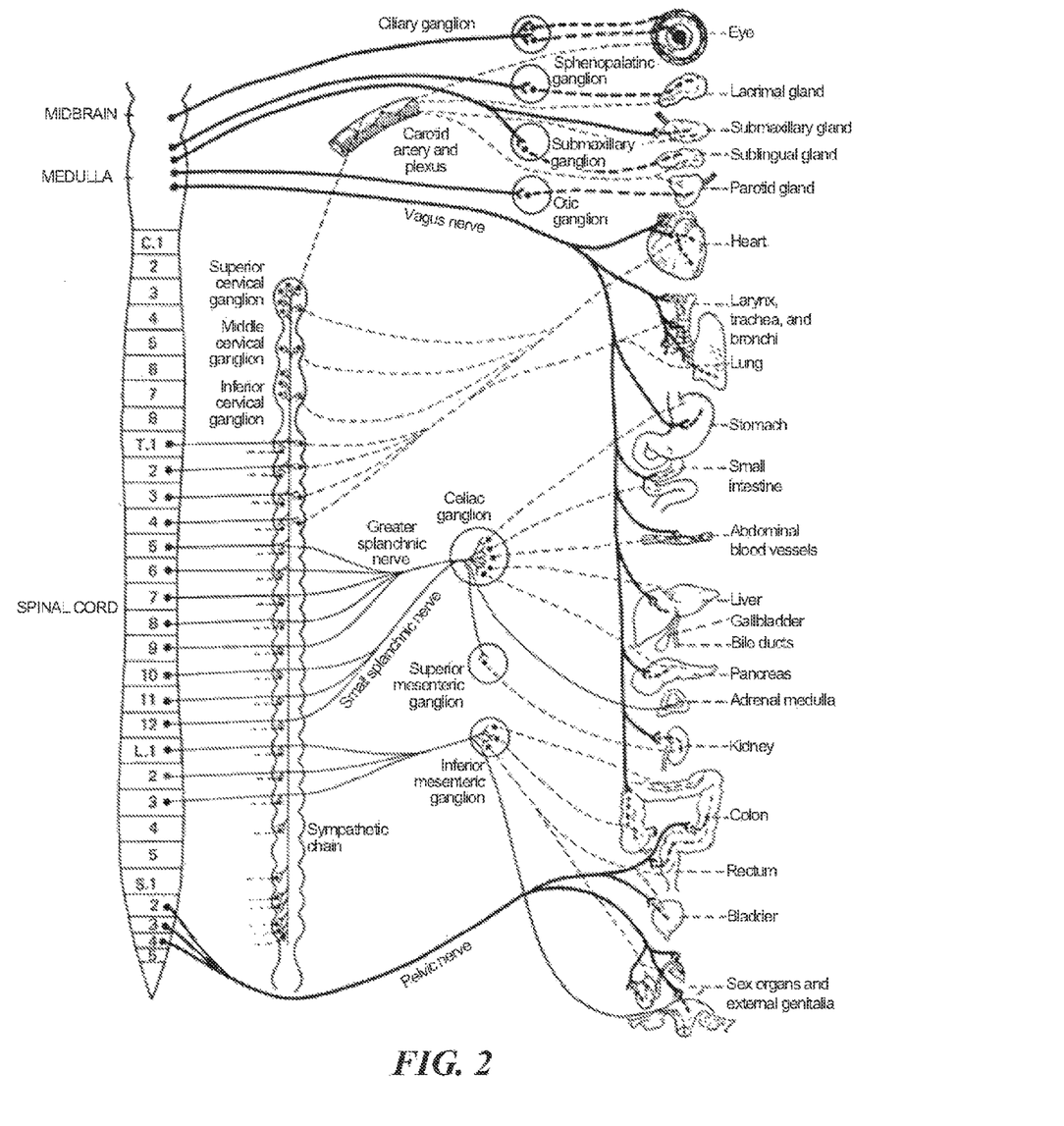
FIG. 2 is a conceptual illustration of the sympathetic nervous system (SNS) and how the brain communicates with the body via the SNS.

FIG. 2 is a conceptual illustration of a human SNS illustrating how the brain communicates with the body via the SNA. The nerves comprising the SNS enable bidirectional signal communication between the brain, spinal cord, and nearly every organ system. For example, signals from the periphery to the brain, termed afferent signals, travel within one neuron and carry information primarily about, temperature or pain. In the opposite direction, efferent signals are primarily transmitted by a two neuron system; the first neuron originates in the brain and spinal cord, exits at the mid-lower back at spinal levels T1-L2 (the sympathetic thoracolumbar outflow) and synapses in a ganglia. The most prominent ganglia are those found parallel to the vertebral column at spinal levels T1-L2. These are grouped together as the sympathetic trunk. Post-ganglionic nerves from the sympathetic trunk primarily regulate the abdominal and thoracic visceral organs. Other important ganglia of the SNS include the cervical ganglion (regulates organs in the head and thorax), the celiac ganglion, and the mesenteric ganglia (regulates abdominal organs) Post-ganglionic nerves then transmit the signal directly to the peripheral organs.

Efferent neuronal signaling in the SNS is carried by two primary small molecule neurotransmitters; acetylcholine and norepinephrine. All preganglionic signals are mediated by acetylcholine, a chemical messenger that binds and activates cholinergic receptors on postganglionic neurons. Acetylcholine is primarily an activating neurotransmitter. In the brain, for example, acetylcholine improves attention, enhances sensory perceptions, and enhances memory and learning. Preganglionic release of acetylcholine stimulates postganglionic neurons, thereby promoting generation of electric potentials in the postganglionic neurons. Once stimulated, postganglionic neurons primarily use the neurotransmitter noradrenaline (norepinephrine). Norepinephrine binds to adrenergic receptors to directly stimulate peripheral organs. In the adrenal gland, SNS stimulation causes norepinephrine release into the blood, heightening the body's arousal and enhancing the SNS response.

Figure 3:
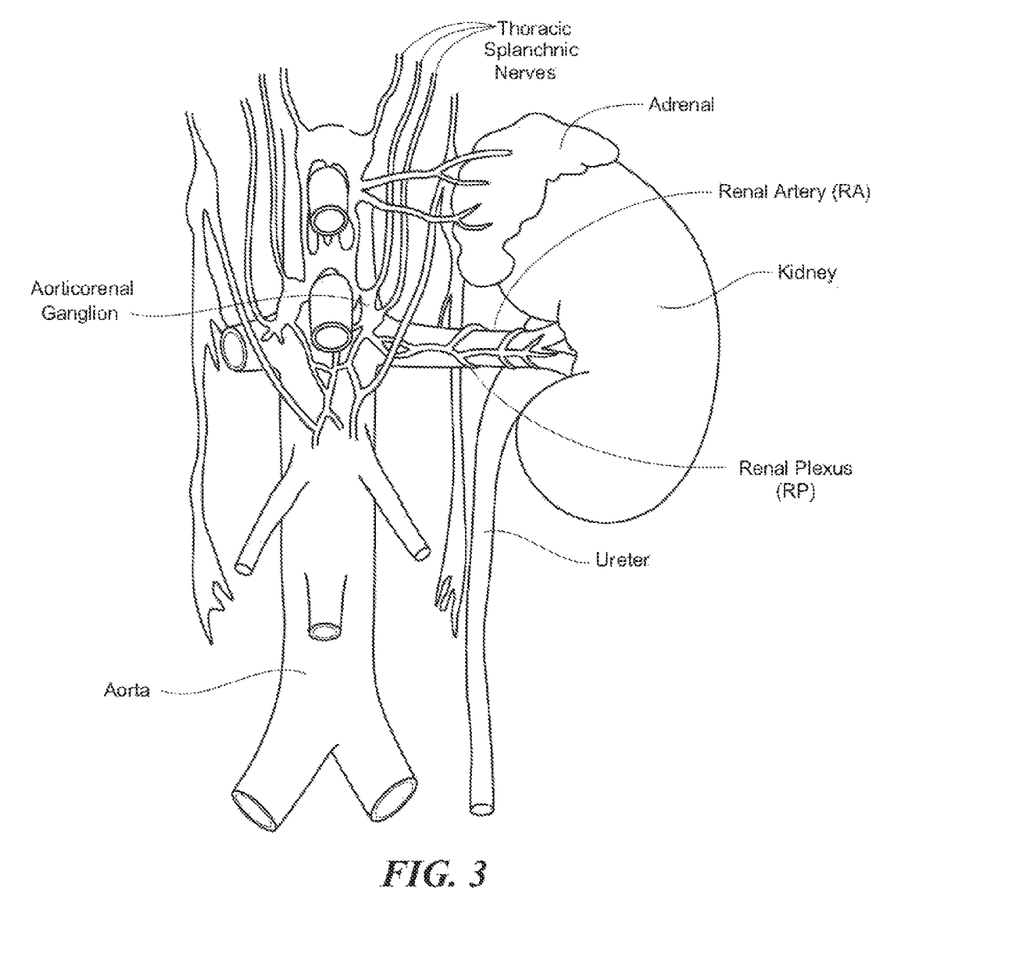
FIG. 3 is an enlarged anatomic view of nerves innervating a left kidney to form the renal plexus surrounding the left renal artery.

FIG. 3 is an enlarged anatomic view of nerves innervating a left kidney to form a renal plexus surrounding the left renal artery. Sympathetic communication between the CNS and the kidney is achieved via many neurons that travel from the sympathetic chain to innervate the kidney. Many of these nerves arise primarily from the celiac ganglion, the superior mesenteric ganglion, and the aorticorenal ganglion. From the ganglia, these fibers join together into a plexus of nerves that surround the renal artery. This is typically termed the renal plexus or renal nerve. The renal plexus or renal nerve is embedded within the adventitia (i.e., the outer wall) of the renal artery extending along the renal artery until it arrives at the substance of the kidney. There is also rich innervation of the kidney vasculature and of the tubular structures (nephrons) that comprise the filtering and concentrating functions of the kidney.

The renal plexus carries both afferent and efferent signals. As mentioned previously, afferent signals increase with temperature, pain, decreased renal blood flow, and intra-renal pathologies such as kidney hypoxia or ischemia. They are also influenced by the chemical composition of the urine; small signaling molecules such as adenosine are released into the urine when the kidneys are hemodynamically (i.e. too much or too little blood flow) or metabolically stressed. Afferent signals are carried by several different neurotransmitters including substance P, a molecule well known to participate in pain signaling. Signals from one kidney impact the renal sympathetic outflow and the functioning of both that kidney and the opposite (contralateral) kidney and also affect the brain. Central integration of the afferent signals in the posterior hypothalamus of the brain and in the spinal cord causes increased central sympathetic outflow.

Efferent renal nerve activity is stimulated by numerous inputs. As mentioned above, afferent signals from one kidney can cause increased efferent activity in that kidney as well as the contralateral kidney. This latter effect is known as the renorenal reflex. In addition, most stimuli of central sympathetic outflow also increase efferent renal nerve activity. These stimuli include infection, inflammation, and acute stress, which release chemical mediators that can act directly on the brain to increase central sympathetic outflow. In addition, feedback mechanisms such as the baroreceptor reflex can increase central sympathetic outflow. Baroreceptor sensors in the carotid arteries of the neck are sensitive to blood pressure. A fall in blood pressure causes a corresponding fall in baroreceptor activity, which stimulates increased sympathetic outflow.

C. Dyspnea

The most rigorous physiologic definitions of dyspnea capture the concept that afferent signals from peripheral or central chemoreceptors ascend to the brain. Afferent neurons significant in dyspnea arise from a large number of sources including the carotid bodies, medulla, lungs, and chest wall. Chemoreceptors in the carotid bodies and medulla supply information regarding the blood gas levels of $O_2$, $CO_2$ and $H^+$. In the lungs, juxtacapillary (J) receptors are sensitive to pulmonary interstitial edema, while stretch receptors signal bronchoconstriction. Muscle spindles in the chest wall signal the stretch and tension of the respiratory muscles. Thus the following conditions may contribute to a feeling of dyspnea: (a) poor ventilation leading to hypercapnia; (b) left heart failure leading to interstitial edema (impairing gas exchange); and (c) asthma causing bronchoconstriction (limiting airflow) and muscle fatigue leading to ineffective respiratory muscle action. Thus, dyspnea is attributed to inadequate respiration (failure to remove $pCO_2$ from blood), increased interstitial lung water content or alveolar water content causing increased lung stiffness and pulmonary edema respectively, lung stiffness of any etiology causing stimulation of interstitial pulmonary j nerve fibers.

Another phenomenon that is associated with or that may contribute to dyspnea is an altered sensitivity of chemoreceptors. For example, altered chemoreceptor sensitivity may manifest as a change in the set point of the chemoreceptor (point at which afferent signals begin and dyspnea is sensed). This changed set point would result in a gain in respiratory effort, which is associated with dyspnea (hypothalamic integration of the signal with efferent signals to the respiratory tree). It has been demonstrated that $pCO_2$ sensitivity may be heightened in patients having certain disease states (e.g. diabetics with autonomic neuropathy). However, in the absence of a tool to modify set point and gain, the idea that heightened sensitivity to $pCO_2$ could be corrected has previously remained untested.

iii. Measuring Sympathetic Activity

SNS activity is often measured using methods including microneurography or norepinephrine spillover. Microneurography is the more direct method of the two to measure the level of sympathetic activity. It involves insertion of an electrode into the nerve to measure directly the action potentials from axons of sympathetic nerves. The electrode picks up signals from all neurons in the nerve bundle. An increased number and frequency of action potentials correlates with higher sympathetic outflow in that nerve bundle. Because this method requires a macroscopic nerve bundle into which the electrode can be placed, it cannot be used to represent the sympathetic stimulation to whole organs, which are often innervated by multiple nerves arranged in a mesh-like plexus. Nevertheless, this method is well suited for measurement of sympathetic stimulation to peripheral muscles, which are often innervated by a single identifiable nerve. When microneurography is used in this case, the technique and measurable quantity is often termed. "muscle sympathetic nerve activity," or MSNA.

Measurement of norepinephrine spillover is a less direct method of estimating SNS activity, but can be used to aggregate SNS outflow to whole organs and in the body as a whole. This method involves measuring the levels of the neurotransmitter norepinephrine released at a target organ. Increased neuronal firing corresponds with increased release of the neurotransmitter norepinephrine, which then can be measured via arterial and venous sampling of norepinephrine (a radioisotope of norepinephrine is also commonly used). For example, samples of blood from the renal artery can be measured for norepinephrine content and compared to the norepinephrine content in samples taken from the renal vein. Higher norepinephrine levels in the venous sample represent increased efferent sympathetic signaling to the kidney.

Overall sympathetic activity is estimated by measuring norepinephrine levels in the central veins draining from the body into the heart, termed "whole body norepinephrine levels." It can be especially useful to measure norepinephrine spillover in specific organs as sympathetic outflow is non-uniform and can vary significantly to different organs. While the above described methods can provide fairly accurate assessments of elevated central sympathetic tone, these methods are not utilized often because of the invasiveness, inconvenience and cost associate with such tests.

IV. Chronic Sympathetic Activation in Dyspnea

While acute activation of the SNS is an appropriate response to maintaining survival, chronic sympathetic activation is a maladaptive response. Without being bound by theory, it is thought that sensory afferent signals originating from the kidneys are often major contributors to initiate and sustain elevated central sympathetic outflow. With chronic stimulation, the body sets a new homeostasis where higher SNS outflow is the norm. This new homeostasis, however, is harmful to the body. Malfunction of the renal sympathetic nervous system and chronic sympathetic activation play a key role in the development and progression of diseases such as essential hypertension, chronic kidney disease, heart failure, insulin resistance, metabolic syndrome and diabetes, among others.

Abnormal sensitivity to $pCO_2$ (set point and/or gain) as well as increased sympathetic nerve activity are seen together in multiple disease states. This correlation suggests that $pCO_2$ sensitivity may be under central autonomic influence. More specifically, this correlation suggests that changes in set point of chemoreceptors may be linked to central sympathetic state, and, for example, increased central sympathetic drive itself may cause increased chemoreceptor sensitivity to partial pressure of carbon dioxide ($pCO_2$) and respiratory muscle response to afferent signaling from these chemoreceptors.

V. Therapeutic Renal Neuromodulation

The physiology described above suggests an integral role between central sympathetic activity and the renal nerves in the development of dyspnea. It is accordingly expected that renal neuromodulation, e.g., via denervation of tissue containing, renal nerves, may be valuable in the treatment of this disease. More specifically, neuromodulation of afferent sensory nerves can reduce the systemic sympathetic drive through direct effect on the brain, thus altering chemosensor sensitivity to $pCO_2$.

Medtronic Ardian LLC has discovered that reduction of sympathetic neural activity in nerves that innervate a kidney of a patient with hypertension can lower blood pressure. For example, sympathetic neural activity can be blocked or reduced by creating thermal lesions of at least a portion of renal sympathetic nerves. This procedure may provide relief of hypertensive conditions by reducing central sympathetic tone in patients having hyperactive central sympathetic tone. Similarly, such a procedure could also correct or improve sensitivity to $pCO_2$ by reducing central sympathetic tone. This could reduce subjective dyspnea that is concomitant with various disease states, for example and not limited to systolic heart failure, diastolic heart failure, congestive heart failure, panic disorders, chronic and acute lung diseases, chronic and acute renal diseases, central sleep apnea, and deconditioning.

Medtronic Ardian LLC has further developed systems and associated methods to selectively modulate the renal afferent and efferent sympathetic nerves that lie within and alongside the adventitia (i.e., outer wall) of the renal arteries. Modulation of such nerves may be achieved using a variety of techniques. For example, the purposeful application of energy (e.g., electrical energy, thermal energy) to tissue can initiate renal neuromodulation via denervation caused by irreversible electroporation, electrofusion, apoptosis, necrosis, ablation, cryogenic ablation, thermal alteration, alteration of gene expression, or another suitable modality.

Figure 4:
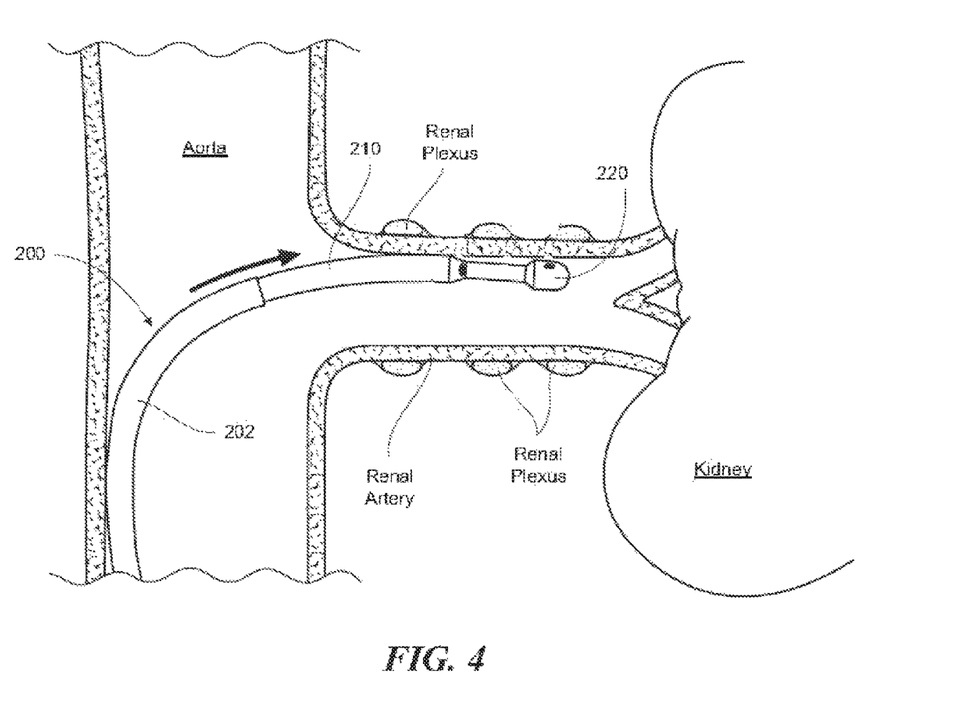
FIG. 4 is a partially schematic view of a catheter-based treatment device positioned within a renal artery and configured for therapeutic renal neuromodulation in accordance with an embodiment of the technology.

Several embodiments of this procedure involve discrete, low-dose radiofrequency ablation of the target nerves via a radiofrequency (RF) emitting catheter placed on the inside wall of the renal artery. FIG. 4, for example, is a detailed anatomic view of a catheter-based treatment device 200 positioned within a renal artery of a patient and configured for renal neuromodulation in accordance with one embodiment of the disclosure. The device 200 can be deployed using a conventional guide catheter or pre-curved renal guide catheter 202. The device 200 can be introduced via the guide catheter 202 through the common femoral artery or, alternatively, through a brachial/radial approach, and advanced to the renal artery under guidance (e.g., fluoroscopic imaging guidance).

A flexible, controllable elongated shaft 210 of the treatment device 200 carries an energy delivery element 220 (e.g., a thermal heating element) and energy can be applied via the energy delivery element 220 to one or more target treatment sites along a length of the renal artery. The target treatment sites can be spaced longitudinally and rotationally along the length of the renal artery. Individual treatments can include, for example, ramped low power RF energy delivery (e.g., about 5 to 8 watts) for a selected period of time (e.g., two minutes). Blood flow through the renal artery can help minimize surface and/or endothelial injury to the target treatment sites. Further, focal ablations spaced apart from each other along the vessel allow for rapid healing. In one embodiment, up to six treatments are applied along the length of the renal artery beginning from where the renal artery branches off the aorta and ending at the kidney itself. In other embodiments, however, a different number of treatments may be applied and the treatment sites may have a different arrangement relative to each other. After all the treatments are completed, the treatment device 200 is removed from the patient. Various embodiments of methods, apparatuses, and systems for performing renal neuromodulation are described in greater detail in U.S. patent application Ser. No. 12/545,648, filed Aug. 21, 2009, and Patent Cooperation Treaty (PCT) Application No. PCT/US09/69334, filed Dec. 22, 2009, both of which are incorporated herein by reference in their entireties.

Other techniques or approaches for renal neuromodulation may also be administered to achieve the therapeutic benefits described herein. For example, renal neuromodulation can be achieved via a pulsed electric field or intravascular electroporation. In still another example, U.S. Pat. No. 6,978,174 describes neuromodulation via delivery of neuromodulatory agents. In yet another example, U.S. Pat. No. 7,620,451 describes neuromodulation via an intra-to-extravascular approach. These patent references are incorporated herein by reference in their entireties.

A. Therapeutic Renal Neuromodulation in the Treatment of Subjective Dyspnea

The recognition that feelings of dyspnea may be substantially a result of altered chemoreceptor sensitivity could change clinical understanding of the many diseases where quality of life is impacted by this subjective symptom. Interestingly, it is exactly this subjective symptom that plays so heavily into quality of life measures and the grading of severity of disease states. For example, in heart failure, the New York Heart Association's functional classification of disease severity is entirely based on subjective classification of dyspnea at rest, with moderate exertion, with mild exertion or without dyspnea. While the functional classification has provided the basis for separation of morbidity and mortality curves, the failure to recognize a common basis or physiologic basis for its etiology has been frustrating, leading to the development of alternative tests, such as peak $VO_2$ during exercise. Nonetheless, hospitalization and clinical decisions are often predicated on failure or success in treatment of dyspnea. Similarly, in all forms of heart failure, panic disorders, chronic kidney diseases, and many chronic lung diseases, subjective dyspnea and subsequent hyperventilatory response underlie the disease pathology.

Clinical efforts have been focused on changing underlying ventricular function in heart failure, congestion status in heart failure, dialysis frequency in end stage renal disease (ESRD) and breathing dynamics in chronic lung disorders. However, subjective dyspnea may be principally a neurologic consequence to heightened central sympathetic drive. Consequently, it is expected that subjective dyspnea could be modified with correct therapy targeting the underlying sympathetic hyperactivity. The potential impact of this invention is that the basis of treatment for the aforementioned associated diseases could be altered.

Proposed herein s the idea that dyspnea is a consequence of heightened central and peripheral chemoreceptor sensitivity to $pCO_2$, which is under central sympathetic control. The consequence of this relation is that a therapeutic change in the set point ($pCO_2$ level at which dyspnea is sensed) and/or the gain (minute ventilatory change in response to exposure to $pCO_2$) could be achieved if central sympathetic tone is altered. As previously discussed this may be achieved with therapeutic renal neuromodulation.

B. Measuring Minute Ventilation/$pCO_2$ as an Indicator of Central Sympathetic Drive in Conjunction with Therapeutic Renal Neuromodulation Central hypercapnic chemosensitivity may be assessed with a test that involves breathing air with varying percentages of $CO_2$ and comparing the responding drive to breath. An example of such test may include having a patient rebreath air into a bag (e.g., a 6 liter bag) for a predetermined period of time (e.g., about 4 minutes). The air in the bag 500 may contain a gas mixture of, for example, about 7% $CO_2$ in the beginning of the test rising to about 10% at the end of the test. Measurements of gas contents (e.g., $pCO_2$, % $CO_2$, in exhaled or inhaled gas) and tidal volume (e.g., minute ventilation) may be monitored continuously or intermittently using a gas analyzer 501 (e.g., a Beckman LB-2 $CO_2$ analyzer, available from Beckman Coulter of Brea, Calif.) and flow meter 502 (e.g. a Series 3800 pneumotach, available from Han Rudolph, Inc. of Shawnee, Kans.) (see FIG. 5). Other examples of equipment that may facilitate monitoring $pCO_2$ include suitable capnography and capnometry devices. These devices provide both waveform (capnograph) and digital readout or end-tidal $CO_2$. Most of the commonly used capnography and capnometry devices utilize infrared absorption of $CO_2$ as a principle of operation. The relationship between ventilation and $pCO_2$ may be expressed in terms of volume of breathed air per unit time per unit of partial pressure of $CO_2$ (e.g. liters per minute per millimeters of mercury). A plot of this relationship may characterize a patients sensitivity to $pCO_2$. Such a test assesses hypercapnic ventilator response.

Figure 5:
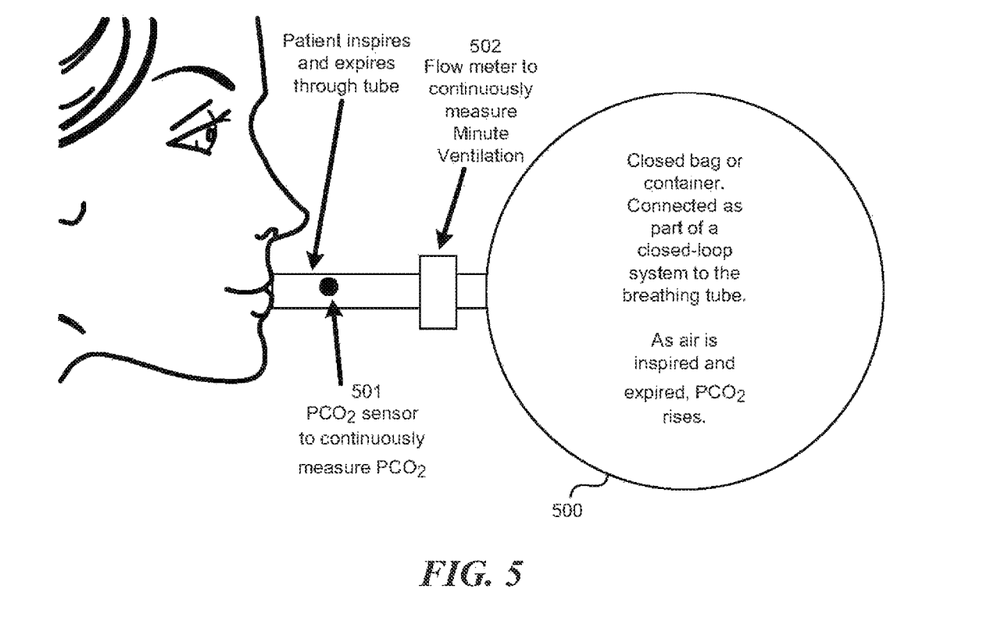
FIG. 5 is a schematic diagram illustrating a test apparatus to monitor ventilator response to $pCO_2$ in accordance with an embodiment of the technology.

A similar apparatus may be modified to measure mouth occlusion pressure, which may be an alternative or additional indication of drive to breathe. For example, in addition the above mentioned apparatus used to measure minute ventilation vs. $pCO_2$, a mouth valve (e.g., a nasal and mouth breathing mask available from Han Rudolph, Inc. of Shawnee Kans.) may separate expiratory flow and inspiratory flow. The expiratory flow may pass through the flow meter and gas analyzer to measure minute ventilation vs. pCO2 and then be returned to the breathing circuit. The inspiratory side of the circuit may be silently occluded during exhalation, and the mouth occlusion pressure may he measured by a pressure sensor a short time (e.g., about 100 msec) after the start of an inspiratory effort against the completely occluded airway periodically (e.g., about every 8-15 breaths). The airway may he reopened once a pressure measurement is taken so breathing can resume.

Figure 6:
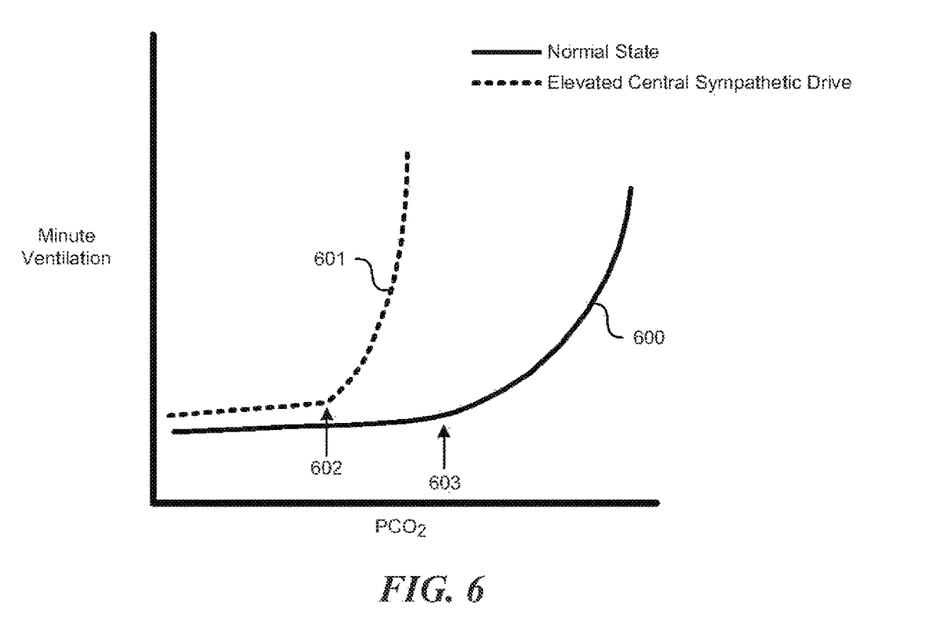
FIG. 6 is a display diagram illustrating ventilator response to $pCO_2$ for elevated and normal central sympathetic drives in accordance with an embodiment of the technology.

A plot of ventilator response (i.e., minute ventilation and/or mouth occlusion pressure) to inhaled $pCO_2$ is expected to show distinct characteristics for various states of central sympathetic drive. For example, as shown in FIG. 6, a patient with a normal central sympathetic drive may demonstrate a $pCO_2$ sensitivity characterized by the solid line 600, while a patient with an elevated central sympathetic drive may demonstrate a $pCO_2$ sensitivity characterized by the dotted line 601. These plats may identify various aspects of a patient's sensitivity to $pCO_2$. For example, a set point (i.e., a level of $pCO_2$ at which afferent signals begin and dyspnea is sensed) may be indicated by an upward inflection point in the plot at 602 and 603; gain in respiratory effort associated with dyspnea may be represented by an increase in minute ventilation and/or mouth occlusion pressure for a given increase in $pCO_2$. Alternatively, ventilatory response vs. $pCO_2$ data may be represented by a linear model and gain may be represented by a slope of the linear plot. Such characteristics may indicate an enhanced chemoreceptor reflex. For example, a patient with a normal sympathetic state may have a hypercapnic ventilatory response in a range of about 1.5 to 3 $L/min/mmHgCO_2$, while a patient with an excited sympathetic state may have a hypercapnic ventilatory response above about 3 $L/min/mmHgCO_2$. Furthermore, a scale of severity of heightened sympathetic state may be correlated to ranges of hypercapnic ventilatory responses (e.g., about 3 to 5 $L/min/mmHgCO_2$ may represent a mildly excited sympathetic state, above 12 $L/min/mmHgCO_2$ may represent a severely excited sympathetic state, and in between may represent progressive severities.)

Data from the sensors may be monitored by software that may record, process, analyze, and display information about a patient's hypercapnic ventilator response. Non-limiting examples of how software may be implemented follow: Software may analyze flow rate of a breath and characterize various phases of the respiratory cycle; end tidal values of $pCO_2$ may be isolated by correlating the $pCO_2$ measurements with the phases of a respiratory cycle; outlier data may be filtered out, for example when a patient coughs or swallows; repeat tests could be averaged or compared; a patient's test results could be stored and retrieved at a later date or compared to another test; data may be analyzed to create best fit curves or plots, for example with linear regression analysis; plots can be displayed on a graph or numerically; results can be displayed with comparison to normal ranges of ventilatory response; evaluation of results may be displayed showing if a patient has normal, heightened or along a scale of $pCO_2$ sensitivities or sympathetic drive. Such software may be provided as an installation program to be installed on a computer or laptop or the software may be provided in a computerized medical device.

The suggestion that ventilator response to inhaled $pCO_2$ may identity heightened central sympathetic tone provides a clinical analogy to the use of muscle sympathetic nerve activity (MSNA). It is possible that one or both could be used for the purpose of diagnosing and/or selecting patients, monitoring success of therapy, or identification of late failures of therapeutic renal denervation. A test for ventilator response to inhaled $pCO_2$ could be easier to administer, require simpler and cheaper test equipment, and be less stressful to the patient compared to an MSNA test or a norepinephrine spillover test.

The concept is that, like MSNA, elevated hyperventilatory response to inhaled $pCO_2$ may represent elevated central sympathetic state, a condition that could be important for the success of renal denervation for the treatment of several disease states. Thus, the test might be used to screen candidates for a renal denervation procedure. In one embodiment, for example, a patient who has a disease state, such as hypertension, but does not show an elevated central sympathetic state as determined by a test that compares minute ventilation to $pCO_2$ may not be a suitable candidate for a renal denervation procedure. However, a patient that tests positive fur elevated central sympathetic state using a $pCO_2$ sensitivity test may be more likely to have a therapeutic response to renal denervation. Similarly, when performed after a renal denervation procedure, it is expected that a $pCO_2$ sensitivity test may be a tool to assess success of initial denervation and/or subsequent monitoring of late failure of the therapy.

Knowing that treatment has not successfully altered chemoreceptor function does not necessarily imply that the treatment failed (it is possible that additional factors are operative in coordinating respiratory response to inhaled $pCO_2$). Further, it is possible that the treatment was only partially successful, which may suggest the potential for a repeat renal denervation treatment.

VI. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The disclosure may be defined by one or more of the following clauses:

1. A method of treating a human patient diagnosed with dyspnea, the method comprising:
   at least partially inhibiting sympathetic neural activity in nerves that innervate a kidney of the patient; and
   reducing central sympathetic drive in the patient in a manner that treats the patient for the dyspnea.

2. The method of clause 1 wherein reducing central sympathetic drive in a manner that treats the patient for the dyspnea comprises reducing the patient's sensitivity to $pCO_2$.

3. The method of clause 1 wherein reducing central sympathetic drive in a manner that treats the patient for the dyspnea comprises altering the patient's chemoreceptor set point.

4. The method of clause 1 wherein reducing central sympathetic drive in a manner that treats the patient for the dyspnea comprises changing the patient's gain in respiratory effort associated with increased $pCO_2$.

5. The method of clause 1 wherein the dyspnea is associated with a condition comprising at least one of systolic heart failure, diastolic heart failure, congestive heart failure, panic disorders, chronic lung disease, acute lung disease, renal disease, deconditioning, and hypertension.

6. The method of clause 1 wherein the dyspnea comprises subjective feelings of breathlessness.

7. The method of clause 1 wherein at least partially inhibiting sympathetic neural activity in nerves that innervate a kidney of the patient comprises ablating a renal nerve of the patient with an energy transfer element positioned at least proximate to the renal nerve.

8. The method of clause 7 wherein ablating a renal nerve comprises thermally ablating the renal nerve.

9. The method of clause 8 wherein thermally ablating the renal nerve comprises necrosing the renal nerve via a cryoablation device.

10. The method of clause 8 wherein thermally ablating the renal nerve comprises delivering an energy field to the renal nerve via the energy transfer element.

11. The method of clause 7 wherein ablating a renal nerve comprises ablating the renal nerve via an intravascularly positioned catheter carrying the energy transfer element.

12. The method of clause 11 wherein ablating the renal nerve via an intravascularly positioned catheter comprises ablating the renal nerve via the energy transfer element from within a renal artery of the patient.

13. The method of clause 1 wherein at least partially inhibiting sympathetic neural activity in nerves that innervate a kidney of the patient comprises blocking afferent neural activity.

14. The method of clause 1 wherein at least partially inhibiting sympathetic neural activity in nerves that innervate a kidney of the patient comprises blocking efferent neural activity 15. A method of determining whether a human patient will respond to a renal denervation treatment, the method comprising:
   measuring $pCO_2$ sensitivity of the patient;
   evaluating a sympathetic drive state of the patient based on the measured $pCO_2$ sensitivity; and based at least in part on the measured $pCO_2$ sensitivity and the evaluation, determining whether the patient is likely to respond to a renal denervation treatment.

16. The method of clause 15 wherein evaluating the sympathetic drive state of the patient comprises comparing the measured $pCO_2$ sensitivity of the patient to a representative $pCO_2$ sensitivity of a patient having relatively normal central sympathetic tone.

17. A method of evaluating effectiveness of a renal denervation procedure to reduce central sympathetic drive, the method comprising:
  measuring a hypercapnic ventilatory response of a patient after the patient has undergone a renal denervation procedure; and
  evaluating a central sympathetic state of the patient based, at least in part, on the hypercapnic ventilatory response.

18. The method of clause 18, further comprising measuring the hypercapnic ventilatory response of the patient prior to administering the renal denervation procedure, and wherein the hypercapnic ventilatory response of the patient following the renal denervation procedure is compared to the hypercapnic ventilatory response of the patient prior to the procedure.

19. A system for determining central sympathetic drive in a patient, the system comprising:
  a breathing tube configured for respiratory communication with the patient;
  a container configured to receive respiratory communication from the patient via the breathing tube;
  a first sensor configured to measure content of air within the breathing tube;
  a second sensor configured to measure a characteristic or parameter associated with respiration of the patient; and
  a component configured to determine a minute ventilation of the patient and plat the determined minute ventilation as a function of measured $pCO_2$ of the patient.

20. The system of clause 19 wherein the first sensor comprises a gas analyzer.

21. The system of clause 19 wherein the first sensor is configured to measure at least one of $CO_2$, $O_2$, $N_2$, $pCO_2$, and $pO_2$.

22. The system of clause 19 wherein the second sensor is configured to measure a characteristic or parameter from a group comprising volumetric flow rate, mass flow rate, and pressure.

23. The system of clause 19, further comprising a third sensor configured to measure content of air in the container.

I claim:

1. A method of treating a human patient diagnosed with dyspnea, the method comprising:
  intravascularly positioning a catheter carrying an energy transfer element within a renal artery and at least proximate renal nerves of the patient with diagnosed dyspnea,
  wherein, before therapy, the patient has a measured hypercapnic ventilatory response above a threshold value of 3 $L/min/mmHgCO_2$;
  ablating the renal nerves of the patient via energy from the energy transfer element,
  wherein ablating the renal nerves at least partially reduces sympathetic neural activity in the renal nerves of the patient; and
  reducing central sympathetic drive in the patient in a manner that treats the patient for the dyspnea and reduces the patient's sensitivity to $pCO_2$ such that the patient has a measured hypercapnic ventilatory response below the threshold value.

2. The method of claim 1 wherein reducing central sympathetic drive in a manner that treats the patient for the dyspnea comprises altering the patient's chemoreceptor set point.

3. The method of claim 1 wherein reducing central sympathetic drive in a manner that treats the patient for the dyspnea comprises changing the patient's gain in respiratory effort associated with increased $pCO_2$.

4. The method of claim 1 wherein the dyspnea is associated with a condition comprising at least one of systolic heart failure, diastolic heart failure, congestive heart failure, panic disorders, chronic lung disease, acute lung disease, renal disease, deconditioning, and hypertension.

5. The method of claim 1 wherein ablating the renal nerves comprises thermally ablating the renal nerves.

6. The method of claim 5 wherein thermally ablating the renal nerves comprises necrosing the renal nerves via a cryoablation device.

7. The method of claim 5 wherein thermally ablating the renal nerves comprises delivering an energy field to the renal nerves via the energy transfer element.

8. The method of claim 1 wherein at least partially reducing sympathetic neural activity in the renal nerves of the patient comprises blocking afferent neural activity.

9. The method of claim 1 wherein at least partially reducing sympathetic neural activity in the renal nerves of the patient comprises blocking efferent neural activity.

10. The method of claim 1 wherein, before therapy, the patient has a measured hypercapnic ventilatory response above 12 $L/min/mm/HgCO_2$.

11. The method of claim 1 wherein, before therapy, the patient has a measured hypercapnic ventilatory response from about 5 $L/min/mm/HgCO_2$ to about 12 $L/min/mmHgCO_2$.

12. The method of claim 1 wherein, before therapy, the patient has a measured hypercapnic ventilatory response above 3 $L/min/mmHgCO_2$ to about 5 $L/min/mmHgCO_2$.

* * * * *